(12) United States Patent
Kiriyama et al.

(10) Patent No.: US 10,705,039 B2
(45) Date of Patent: Jul. 7, 2020

(54) SENSOR FOR DETECTING MAGNETIC POWDERS IN A LUBRICANT

(71) Applicant: NABTESCO CORPORATION, Tokyo (JP)

(72) Inventors: Takeshi Kiriyama, Tsu (JP); Takeshi Nishimura, Tsu (JP); Kazuhiko Sakurai, Tsu (JP); Masaki Harada, Tsu (JP)

(73) Assignee: NABTESCO CORPORATION, Tokyo (JP)

( * ) Notice: Subject to any disclaimer, the term of this patent is extended or adjusted under 35 U.S.C. 154(b) by 179 days.

(21) Appl. No.: 15/935,413

(22) Filed: Mar. 26, 2018

(65) Prior Publication Data

US 2018/0275083 A1    Sep. 27, 2018

(30) Foreign Application Priority Data

Mar. 27, 2017 (JP) .................................. 2017-061877
Jun. 13, 2017 (JP) .................................. 2017-116250

(51) Int. Cl.
*G01N 27/12* (2006.01)
*G01N 33/28* (2006.01)

(52) U.S. Cl.
CPC ......... *G01N 27/12* (2013.01); *G01N 33/2858* (2013.01)

(58) Field of Classification Search
CPC .............. F01M 11/10; F01M 2011/144; F16N 2200/04; F16N 29/00; F16N 2210/14;
(Continued)

(56) References Cited

U.S. PATENT DOCUMENTS 2,462,715 A * 2/1949 Booth ..................... H01F 7/02
                                                200/61.09
3,193,815 A * 7/1965 Prestal ............... G01N 15/0656
                                                340/627
(Continued)

FOREIGN PATENT DOCUMENTS

JP       2005-331324 A      12/2005
JP       2010014520 A  *    1/2010
JP       2011007610 A  *    1/2011  ......... G01N 33/2888

OTHER PUBLICATIONS

Machine Translation of Japanese Patent Application Publication JP-2010007610 A which originally published on Oct. 13, 2011. (Year: 2011).*

*Primary Examiner* — David A Rogers
(74) *Attorney, Agent, or Firm* — Pillsbury Winthrop Shaw Pittman, LLP

(57) ABSTRACT

One object is to increase the amount of abrasion powder accumulated in a sensing region to improve the sensitivity in sensing the abrasion powder. Provided is a sensor for sensing reduction of electric resistance between electrodes, a magnetic field being applied between the electrodes to accumulate magnetic powder floating in a lubricant between the electrodes, wherein at least one sensing region in which the magnetic powder is to be accumulated is provided in at least a part of a region between the electrodes, and the magnetic powder is inhibited from being accumulated in a non-sensing region constituted by a space around the electrodes other than the at least one sensing region.

15 Claims, 20 Drawing Sheets

(58) Field of Classification Search
CPC . F16N 2260/18; F16N 29/04; G01N 33/2888; G01N 33/2858; G01N 27/07
See application file for complete search history.

(56) References Cited

U.S. PATENT DOCUMENTS

| | | | | |
|---|---|---|---|---|
| 3,432,750 A * | 3/1969 | Botstiber | ............... | G01N 27/74 324/439 |
| 4,008,464 A * | 2/1977 | Hobbie | ............... | B60R 16/0232 340/631 |
| 4,030,028 A * | 6/1977 | Allender | ............... | F01M 11/10 324/698 |
| 4,070,660 A * | 1/1978 | Tauber | ............... | G01N 33/2858 340/631 |
| 4,302,754 A * | 11/1981 | Magee | ............... | G01N 33/2858 340/631 |
| 4,323,843 A * | 4/1982 | Batham | ............... | F01M 11/10 200/61.09 |
| 4,598,280 A * | 7/1986 | Bradford | ............... | G07C 3/00 324/698 |
| 5,118,410 A * | 6/1992 | Rumberger | ............ | B01D 35/143 210/243 |
| 5,179,346 A * | 1/1993 | McGee | ............... | G01N 15/0656 324/204 |
| 5,274,335 A * | 12/1993 | Wang | ............... | G01N 33/2888 324/663 |
| 5,384,535 A * | 1/1995 | Mayeur | ............... | B03C 1/282 324/204 |
| 5,402,113 A * | 3/1995 | Naas | ............... | G01N 15/0656 200/61.09 |
| 5,457,396 A * | 10/1995 | Mori | ............... | G01N 15/0266 324/698 |
| 5,596,266 A * | 1/1997 | Mori | ............... | G01N 15/1031 324/446 |
| 5,696,331 A * | 12/1997 | Otsuka | ............... | F16N 29/00 73/865.8 |
| 6,587,050 B2 * | 7/2003 | Owen | ............... | G01R 31/005 324/527 |
| 6,776,261 B2 * | 8/2004 | Eriksen | ............... | F16C 19/52 184/6.4 |
| 6,791,334 B2 * | 9/2004 | Horie | ............... | G01N 27/4166 324/438 |
| 6,810,717 B2 * | 11/2004 | Heremans | .......... | G01N 33/2888 73/53.05 |
| 6,911,830 B2 * | 6/2005 | Heremans | ............... | G01N 27/06 324/698 |
| 7,043,402 B2 * | 5/2006 | Phillips | ............... | G01N 27/02 324/600 |
| 7,112,973 B2 * | 9/2006 | Itomi | ............... | G01N 33/2888 324/698 |
| 7,134,323 B1 * | 11/2006 | Discenzo | ........... | G01N 33/2888 73/53.05 |
| 7,151,383 B2 * | 12/2006 | Itomi | ............... | G01N 33/2888 324/698 |
| 7,729,870 B2 * | 6/2010 | Sun | ............... | G01F 23/265 324/441 |
| 7,918,134 B2 * | 4/2011 | Hedtke | ............... | G01L 27/005 73/718 |
| 8,018,237 B2 * | 9/2011 | Takahashi | ........... | G01N 33/2858 324/204 |
| 8,074,493 B2 * | 12/2011 | Augros | ............... | B03C 1/286 73/61.42 |
| 8,340,928 B2 * | 12/2012 | Sun | ............... | G01F 23/265 324/441 |
| 8,490,465 B2 * | 7/2013 | Ante | ............... | F02D 41/1466 73/23.2 |
| 8,756,026 B2 * | 6/2014 | Flandrois | ............... | F16N 29/00 702/149 |
| 9,448,196 B2 * | 9/2016 | Jackson | ............... | G01N 27/06 |
| 9,588,097 B2 * | 3/2017 | Rohde | ............... | G01N 33/2888 |
| 9,623,350 B2 * | 4/2017 | Rohrbach | ........... | B01D 35/005 |
| 10,215,012 B2 * | 2/2019 | McDonald | ............ | E21B 33/03 |
| 10,359,077 B2 * | 7/2019 | Ito | ............... | F16C 19/383 |
| 2002/0113596 A1 * | 8/2002 | Horie | ............... | G01N 27/4166 324/438 |
| 2003/0221911 A1 * | 12/2003 | Eriksen | ............... | F16C 19/52 184/6.4 |
| 2005/0212533 A1 * | 9/2005 | Itomi | ............... | G01N 33/2888 324/698 |
| 2008/0289400 A1 * | 11/2008 | Quist | ............... | G01N 11/16 73/54.01 |
| 2009/0320567 A1 * | 12/2009 | Takahashi | ........... | G01N 33/2858 73/53.07 |
| 2011/0011154 A1 * | 1/2011 | Ante | ............... | F02D 41/1466 73/23.33 |
| 2012/0046896 A1 * | 2/2012 | Flandrois | ............... | F16N 29/00 702/65 |
| 2014/0083172 A1 * | 3/2014 | Rohde | ............... | G01N 33/2858 73/53.05 |
| 2014/0246380 A1 * | 9/2014 | Rohrbach | ........... | B01D 35/005 210/748.16 |
| 2016/0003755 A1 * | 1/2016 | Jackson | ............... | G01N 27/06 324/693 |
| 2016/0363552 A1 * | 12/2016 | Jackson | ............... | G01N 27/06 |
| 2018/0016889 A1 * | 1/2018 | Mcdonald | ............ | E21B 33/03 |
| 2018/0223907 A1 * | 8/2018 | Ito | ............... | F16N 29/04 |

\* cited by examiner

SENSOR FOR DETECTING MAGNETIC POWDERS IN A LUBRICANT

CROSS-REFERENCE TO RELATED APPLICATIONS

This application is based on and claims the benefit of priority from Japanese Patent Application Serial Nos. 2017-061877 (filed on Mar. 27, 2017) and 2017-116250 (filed on Jun. 13, 2017), the contents of which are hereby incorporated by reference in their entirety.

TECHNICAL FIELD

The present invention relates to a sensor.

BACKGROUND

In a mechanical device such as a speed reducer, a housing that houses mechanical parts such as a gear and a bearing contains a lubricant to prevent damage to the mechanical parts. The lubricant includes an abrasion powder (mainly iron powder) mixed therein as the mechanical parts wear during operation of the mechanical device.

In general, when wear of mechanical parts advances into the wear-out failure period in the failure rate curve (the bathtub curve), a larger amount of abrasion powder (produced from the mechanical parts) is mixed into the lubricant. For preventive maintenance, it is necessary to timely sense the increase of the amount of produced abrasion powder.

For example, Japanese Patent Application Publication No. 2005-331324 ("the '324 Publication") discloses a sensor that senses the amount of metal powder in an oil. The sensor of the '324 Publication includes: a sensor head having a permanent magnet; a cup-shaped electrode provided on a distal end surface of the sensor head; and a plurality of rod-shaped conductive members arranged on an outer peripheral surface of the sensor head. The output of the sensor is varied when a short circuit occurs between the rod-shaped conductive members due to the abrasion powder accumulated between opposed end surfaces of the conductive members and the cup-shaped electrode subjected to a magnetic field by the permanent magnet (a sensing region). In the '324 Publication, the uncleanness of the oil can be sensed by variation of the output of the sensor.

In the '324 Publication, the magnetic flux leaks into spaces around the sensing region to cause the abrasion powder to be accumulated in regions other than the sensing region. Therefore, a small amount of abrasion powder accumulates in the sensing region, resulting in lower sensitivity of the sensor.

SUMMARY

The present invention addresses the above drawback, and one object thereof is to allow efficient accumulation of a magnetic powder such as an abrasion powder in the sensing region thereby to improve the sensitivity of the sensor sensing the magnetic powder.

An embodiment of the present invention provides a sensor for sensing reduction of electric resistance between electrodes, a magnetic field being applied between the electrodes to accumulate magnetic powder floating in a lubricant between the electrodes, wherein at least one sensing region in which the magnetic powder is to be accumulated is provided in at least a part of a region between the electrodes, and the magnetic powder is inhibited from being accumulated in a non-sensing region constituted by a space around the electrodes other than the at least one sensing region.

The above sensor may be configured such that the electrodes include a first electrode and at least one second electrode, at least one gap is provided between the first electrode and the at least one second electrode, and the at least one gap includes the at least one sensing region to which the magnetic field is applied.

The above sensor may be configured such that the first electrode comprises a magnet producing the magnetic field.

The above sensor may further comprise a magnet producing the magnetic field.

The above sensor may further comprise a covering member that covers the electrodes to inhibit the magnetic powder from being accumulated in the non-sensing region.

The above sensor may be configured such that an entire periphery of the magnet is covered with a magnet covering member.

The above sensor may be configured such that the magnetic field is selectively applied to the at least one sensing region.

The above sensor may be configured such that the at least one sensing region comprises a plurality of sensing regions.

The above sensor may be configured such that the plurality of sensing regions comprise a first sensing region and a second sensing region, the first sensing region is provided adjacent to an N-pole of the magnet, and the second sensing region is provided adjacent to an S-pole of the magnet.

The above sensor may be configured such that the at least one second electrode comprises a plurality of second electrodes, the at least one gap comprises a plurality of gaps provided between the first electrode and each of the plurality of second electrodes, and each of the plurality of gaps includes one of the plurality of sensing regions.

The above sensor may be configured such that the plurality of sensing regions have different gap lengths.

The above sensor may comprise a plurality of pairs of the first and second electrodes, wherein the plurality of pairs of the first and second electrodes have different gap lengths.

The above sensor may be configured such that a narrow recess is provided in an outer periphery of the sensor, and the at least one sensing region is provided deep in the recess.

The above sensor may further comprise a filter member disposed between the at least one sensing region and an outer space, the filter member blocking foreign matter having a large particle diameter.

The above sensor may be configured such that magnetic flux is prevented from leaking out of the at least one sensing region.

The above sensor may be configured such that the at least one sensing region is interposed between a first plane formed on the first electrode and a second plane formed on the at least one second electrode and opposed in parallel to the first plane, and magnetic flux intersects the first plane and the second plane perpendicularly in the at least one sensing region.

Advantages

According to an embodiment of the present invention, the magnetic power is inhibited from accumulating in non-sensing regions, and thus it is possible to accumulate the magnetic powder efficiently in the sensing region. As a result, the sensitivity of the sensor is improved, making it possible to sense an increase of the amount of produced abrasion powder reliably (with a high reliability).

DESCRIPTION OF THE EMBODIMENTS

Embodiments of the present invention will now be described with reference to the appended drawings. The following description will be focused on an industrial robot as an example according to an embodiment of the present invention.

Figure 1:
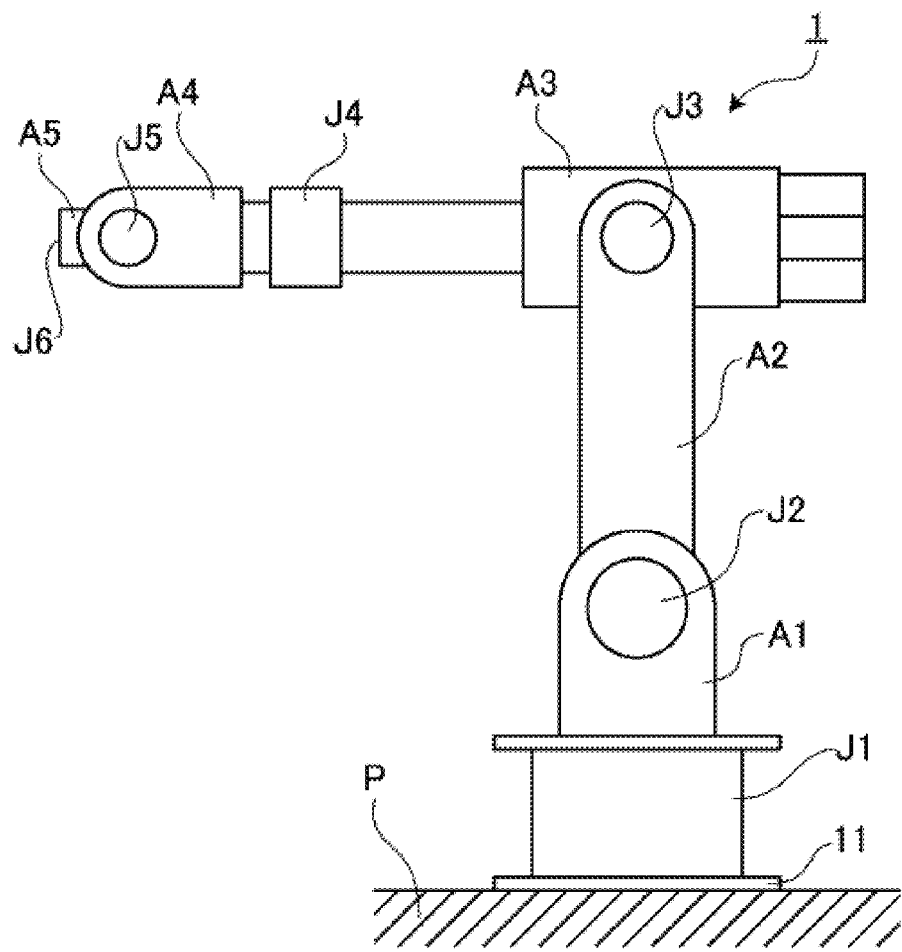
FIG. 1 is a side view of an industrial robot according to an embodiment of the present invention.

FIG. 1 is a side view of an industrial robot 1 according to an embodiment of the present invention. The industrial robot 1 is a vertical articulated robot having six axes.

As shown in FIG. 1, the industrial robot 1 includes a mounting portion 11, arms A1 to A5, and joints J1 to J6. The mounting portion 11 serves to mount the industrial robot 1 on a floor, a wall, a ceiling, or the like. The joint J1 operatively connects between the mounting portion 11 and the arm A1. The joint J2 operatively connects between the arm A1 and the arm A2. The joint J3 operatively connects between the arm A2 and the arm A3. The joint J4 operatively connects between the arm A3 and the arm A4. The joint J5 operatively connects between the arm A4 and the arm A5. On the distal end of the industrial robot 1 (the distal end of the joint J6), there is mounted a hand piece (not shown).

Each of the joints J1 to J6 includes a servo motor for driving and a speed reducer. The joints J1 to J6 have the same basic configuration. Representing the joints J1 to J6, the joint J2 will now be described in detail. As for the joints J1, J3 to J6, the detailed description will be omitted.

Figure 2:
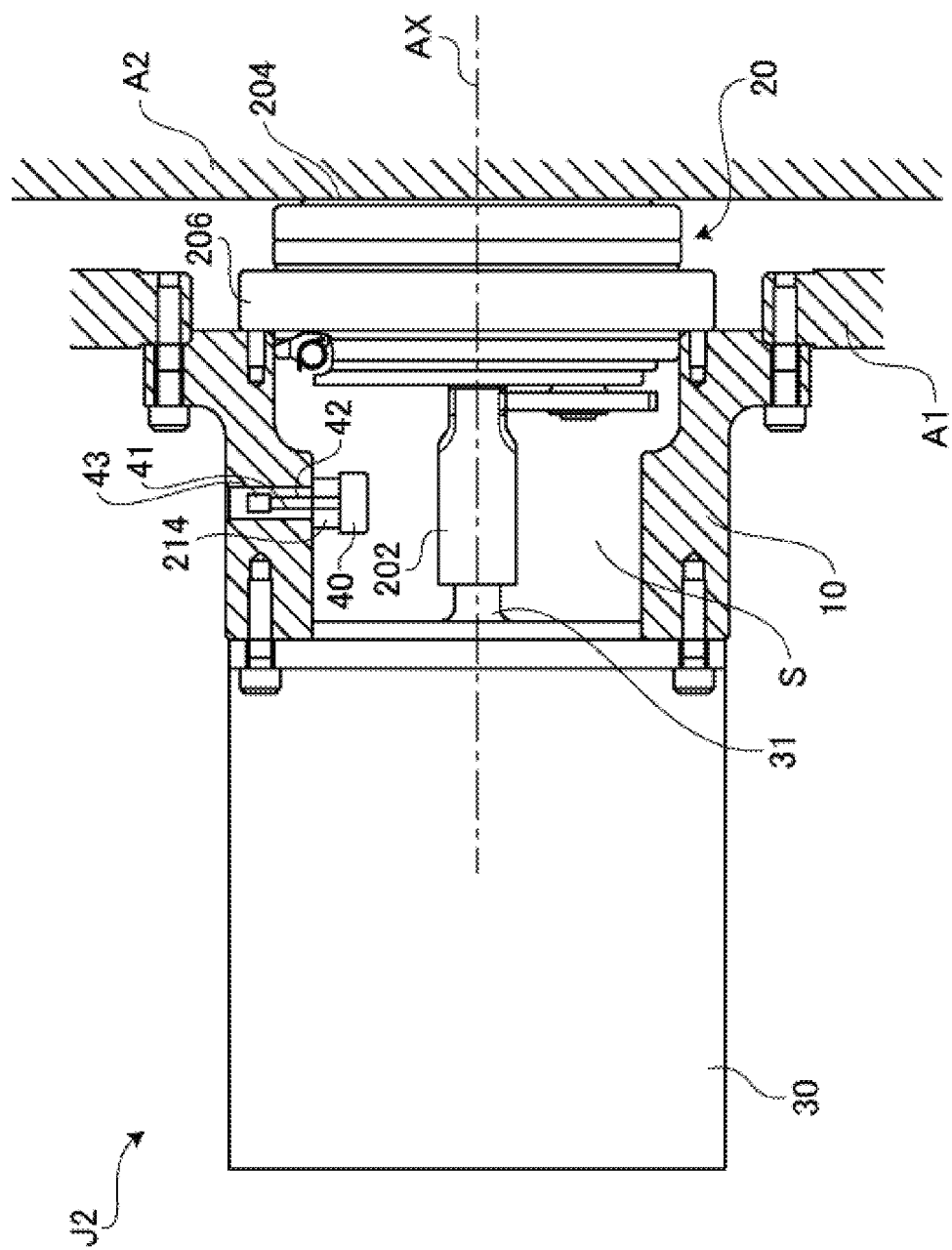
FIG. 2 is a sectional view of a joint portion and surroundings thereof included in an industrial robot according to an embodiment of the present invention.

FIG. 2 is a partially sectional view showing the joint J2 and the vicinity thereof. As shown in FIG. 2, the joint J2 includes a flange 10, a speed reducer 20, and a servo motor 30.

The flange 10 is a frame of the joint J2. The casings of the speed reducer 20 and the servo motor 30 are mounted to the flange 10. The flange 10 is fixed to the arm A1. The flange 10 is a substantially cylindrical member having a hollow portion (a space S). The openings of the flange 10 at both axial ends thereof are blocked by the speed reducer 20 and the servo motor 30, and thus the space S is closed tightly. The space S is filled with a lubricant, and the flange 10 also serves as an oil bath.

The speed reducer 20 includes a casing 206 mounted to the flange 10, an input shaft 202 connected to an output shaft 31 of the servo motor 30, and an output shaft 204 fixed to the arm A2. The input shaft 202 and the output shaft 204 are supported so as to be rotatable around the rotational axis AX relative to the casing 206. An output of the servo motor 30 is input to the speed reducer 20 via the input shaft 202, reduced by the speed reducer 20, and then transmitted to the arm A2 via the output shaft 204. With this arrangement, rotation of the servo motor 30 causes the arm A2 to be rotated around the rotational axis AX relative to the arm A1.

A space in the casing 206 that houses a gear mechanism of the speed reducer 20 communicates with the space S in the flange 10. During operation of the speed reducer 20, rotation of the gear mechanism in the casing 206 causes the lubricant to be circulated between the space in the casing 206 and the space S in the flange 10. As the lubricant is circulated, the abrasion powder produced in the speed reducer 20 is discharged into the space S in the flange 10.

In the space S, a sensor 40 for sensing the increase of the amount of the abrasion powder floating in the lubricant is mounted on a support member 214. The sensor 40 allows the abrasion powder to be accumulated in a gap between electrodes by a magnet and senses the amount of the abrasion powder in the lubricant by a change of electric resistance between the electrodes. There may be a plurality of variations of the sensor 40. FIGS. 3a to 10d show a part of examples of the variations of the sensor 40. It is also possible that the sensor 40 is disposed in the casing 206.

Embodiment 1

Figure 3A:
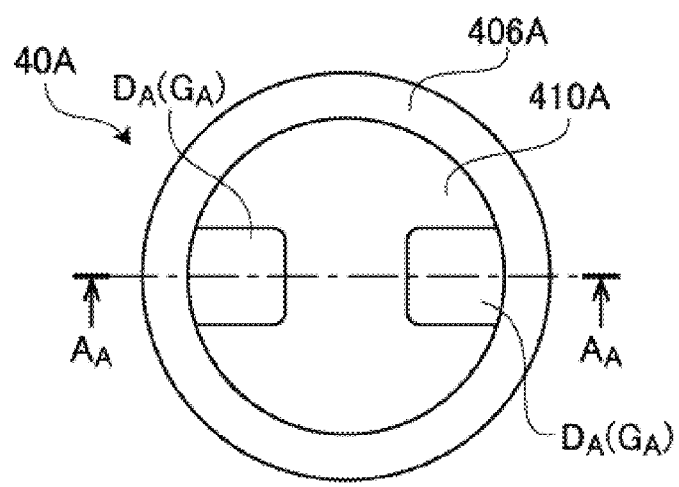
FIGS. 3a to 3e show a sensor according to Embodiment 1 of the present invention.
Figure 3B:
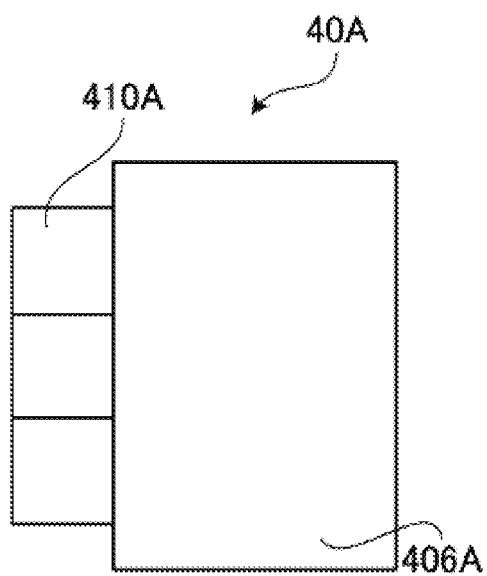
Figure 3C:
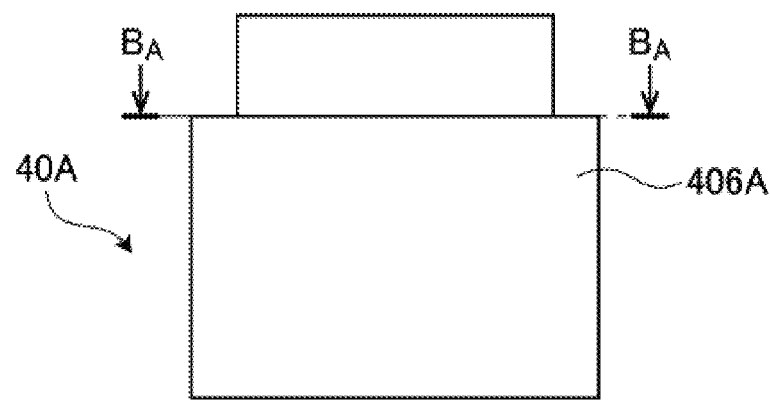
Figure 3D:
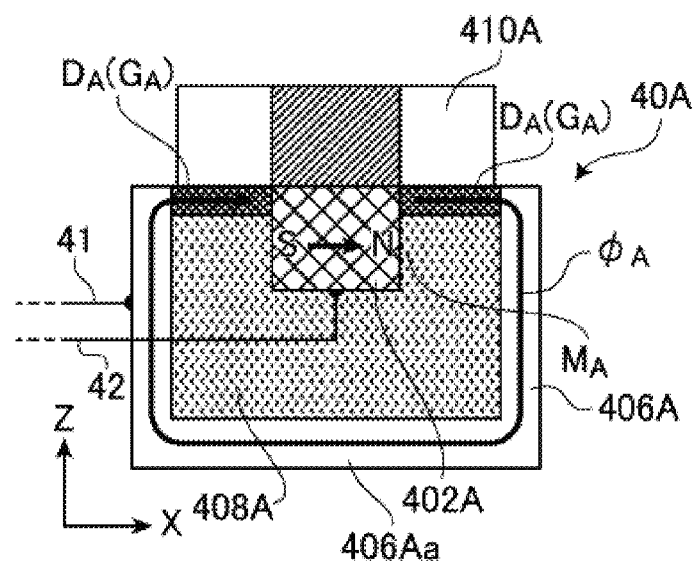
Figure 3E:
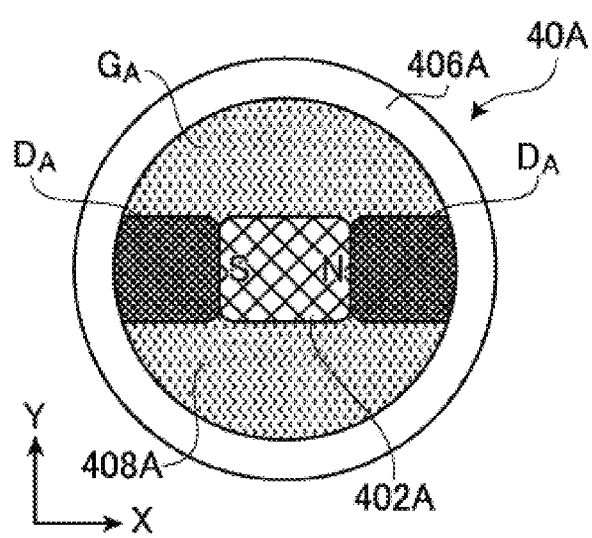

FIGS. 3a to 3e show a sensor 40A according to Embodiment 1 of the present invention. FIGS. 3a, 3b, 3c are a plan view, a right side view, and a front view of the sensor 40A, respectively. FIG. 3d is a sectional view along the line $A_A$-$A_A$ in FIG. 3a. FIG. 3e is a sectional view along the line $B_A$-$B_A$ in FIG. 3c. In the following description, the X-axis direction refers to the left-right direction in FIG. 3e, the Y-axis direction refers to the top-bottom direction in FIG. 3e, and the Z-axis direction (the height direction, or the axial direction) refers to the top-bottom direction in FIG. 3d. The top refers to the top in FIG. 3d (the positive direction in the Z-axis), and the bottom refers to the bottom in FIG. 3d (the negative direction in the Z-axis). In operation, any direction of the sensor 40A may be oriented vertically.

As shown in FIGS. 3a to 3e, the sensor 40A includes a permanent magnet 402A, a box-shaped electrode (an electrode) 406A, a retaining member 408A, and a jacket member 410A. As shown in FIG. 3d, a signal line 41 is connected to the box-shaped electrode 406A, and a signal line 42 is connected to the permanent magnet 402A. Thus, the permanent magnet 402A serves as both a magnet and an electrode.

The box-shaped electrode 406A is a magnetic member formed of a magnetic material having electric conductivity such as iron, ferrite core, or silicon steel. The box-shaped electrode 406A has a substantially cylindrical shape with an opening on one axial end side thereof (the bottom side in FIG. 3d) blocked in the bottom portion 406Aa. Thus, the box-shaped electrode 406A has a cylindrical box-like shape with an opening in the top surface. The box-shaped electrode 406A is not limited to a box-like shape but may be a rectangular parallelepiped opened in only one surface thereof or a polygonal tube with a blocked bottom surface. Further, it is also possible that the electrode 406A is formed of a non-magnetic material such as copper.

In the hollow portion of the box-shaped electrode 406A, there is disposed a retaining member 408A (a covering member) formed of a resin, which is a non-magnetic material (an insulator). The permanent magnet 402A is embedded in the middle of the top portion of the retaining member 408A.

The box-shaped electrode 406A surrounds the retaining member 408A having the permanent magnet 402A embedded therein. The shape of the permanent magnet 402A is not limited to a rectangular parallelepiped but may be a cylinder, a polygonal column, or the like.

As shown in FIG. 3e, the outer shape of the permanent magnet 402A is smaller than the inner periphery of the box-shaped electrode 406A. Therefore, a gap $G_A$ is formed between the permanent magnet 402A and the box-shaped electrode 406A over the entire periphery of the permanent magnet 402A (so as to surround the permanent magnet 402A). In other words, the permanent magnet 402A and the box-shaped electrode 406A face each other with the gap $G_A$ interposed therebetween.

The permanent magnet 402A also serves as an electrode. Each of the permanent magnet 402A and the box-shaped electrode 406A is connected to an output line (the signal lines 41, 42 shown in FIGS. 2 and 3d). In addition, another electrode formed of a magnetic material may be mounted on, for example, the top surface of the permanent magnet 402A. Further, it is also possible that the permanent magnet 402A is a magnet or an electromagnet covered with a non-magnetic material such as copper and the signal line 42 is connected to the non-magnetic material.

The output lines are connected, at the output ends thereof, to a sensor driving circuit (not shown) that monitors the resistance value of the sensor 40A and determines the deterioration of the lubricant from the variation of the resistance value. When the amount of the abrasion powder accumulated in the gap $G_A$ exceeds a predetermined value (the gap $G_A$ is generally filled with the abrasion powder), the electric resistance between the permanent magnet 402A and the box-shaped electrode 406A is lowered (a short circuit occurs), resulting in variation of the output levels of the output lines. The sensor driving circuit senses the deterioration of the lubricant from the lowered electric resistance. It is also possible that the output levels include On signal (with electricity passing) and Off signal (with no electricity passing) for sensing the deterioration of the lubricant between these two states (hereinafter referred to as "the digital sensing").

The sensor driving circuit is connected to a superior control device such as a manipulator in a wired or wireless manner. A circuit board 43 transmits the outputs of the output lines (the outputs of the sensor 40A) to a superior control device either constantly or intermittently (at regular time intervals) for saving electricity.

When sensing the variation of the output level of the output lines received from the circuit board 43, the superior control device gives an alert for demanding maintenance of, for example, the speed reducer 20 by a predetermined notification means (a display or a voice output device).

The permanent magnet 402A is magnetized in the direction of the arrow MA in FIG. 3d. Therefore, the magnetic flux path $\varphi A$ shown in FIG. 3d is formed. In the gap $G_A$ extending over the entire periphery of the permanent magnet 402A, intensive magnetic flux passes through regions positioned in the magnetic flux path. The intensive magnetic flux also passes through regions close to the S and N magnetic poles of the permanent magnet 402A. For convenience in description, these regions are referred to as "the sensing region," and the sensing region of Embodiment 1 is denoted by a sign "$G_A$."

The abrasion powder from the mechanical parts mixed into the lubricant is attracted onto the gap $G_A$ by the magnetism of the permanent magnet 402A.

In particular, the abrasion powder is attracted onto a sensing region $D_A$ that is passed through the intensive magnetic flux. A stable amount of abrasion powder (for example, an amount generally in proportion to the amount of the abrasion powder mixed into the lubricant) is attracted onto the sensing region $D_A$.

There is a large distance from the permanent magnet 402A to the region other than the sensing region $D_A$ (hereinafter referred to as "the non-sensing region") in the gap $G_A$. Therefore, almost no magnetic flux passes through the non-sensing region distant from the permanent magnet 402A, and almost no abrasion powder is attracted onto the non-sensing region.

Thus, in Embodiment 1, the permanent magnet 402A and the gap $G_A$ are disposed in an appropriate positional relationship, so as to set a limited region in the gap $G_A$ as the sensing region $D_A$. Since a stable amount of abrasion powder is attracted concentratedly onto the sensing region $D_A$, the outputs from the sensor 40A are stable. Therefore, the superior control device can sense the increase of the produced abrasion powder reliably (with a high reliability). In case of the digital sensing, the increase of produced abrasion powder is sensed by passing of the electricity, and a sensing signal can be transmitted.

In addition, the magnetic flux is more weak in regions within the gap $G_A$ more distant from the sensing region $D_A$, and the amount of abrasion powder attracted onto such regions is not stable. In other words, the amount of abrasion powder attracted onto such regions is typically not proportional to the amount of the abrasion powder mixed into the lubricant. Since the amount of abrasion powder attracted onto the non-sensing region is instable, such abrasion powder can be a noise to the sensor 40A.

In Embodiment 1, the jacket member 410A (the covering member) made of a resin is mounted on the top of the gap $G_A$ by bonding or other means. The jacket member 410A allows only the sensing region $D_A$ in the gap $G_A$ to be exposed outside. In other words, the jacket member 410A covers the non-sensing region in the gap $G_A$.

Since the jacket member 410A is mounted on the top surface of the gap $G_A$, the distance from the permanent magnet 402A is large in the non-sensing region (or more accurately, the surface of the jacket member 410A positioned above the non-sensing region). Therefore, almost no abrasion powder is attracted onto the outer surface of the jacket member 410A that is distant from the permanent magnet 402A. Accordingly, in Embodiment 1, the region onto which the abrasion power is attracted is substantially limited to the sensing region $D_A$.

In this embodiment, the top surface of the permanent magnet 402A is flush with the top end surface of the box-shaped electrode 406A. Further, the sensor 40A is configured such that the magnetic flux $\varphi_A$ passes in parallel with the top surface of the permanent magnet 402A in the gap $G_A$, by adjusting the shapes, sizes, and arrangements of the permanent magnet 402A and the box-shaped electrode 406A. Therefore, the magnetic flux $\varphi_A$ hardly deviates from the magnetic flux path $\varphi_A$ and leaks out of the sensor 40A. The abrasion powder is restrained by the magnetic flux $\varphi_A$ and accumulated only in the sensing region $D_A$, not on the non-sensing region (the region other than the sensing region $D_A$) in the outer surface of the sensor 40A.

Embodiment 2

Figure 4A:
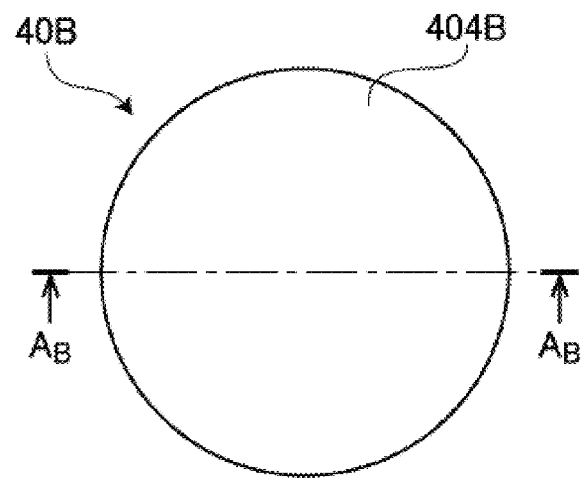
FIGS. 4a to 4d show a sensor according to Embodiment 2 of the present invention.
Figure 4B:
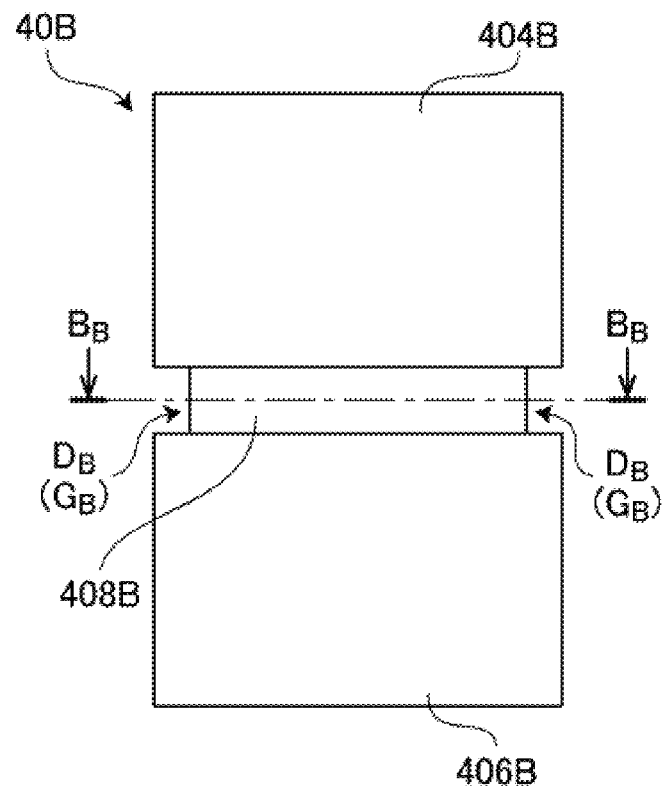
Figure 4C:
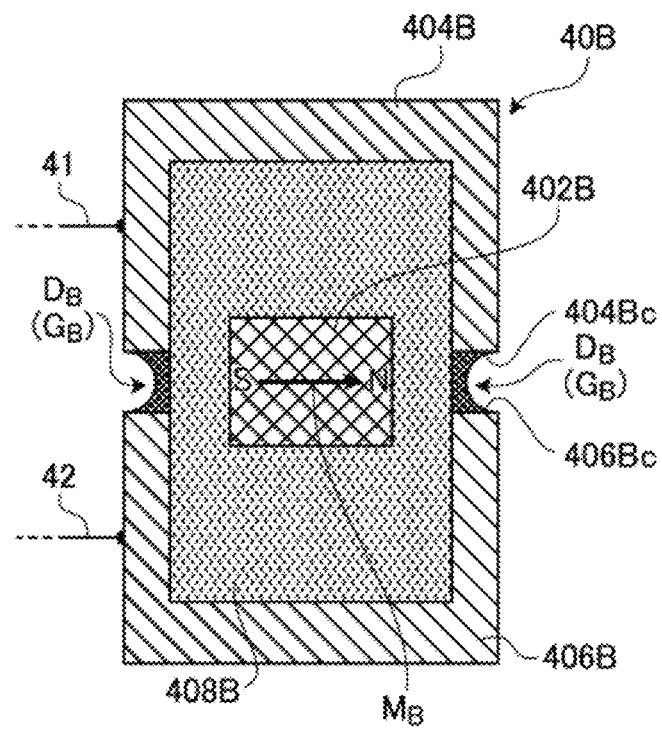
Figure 4D:
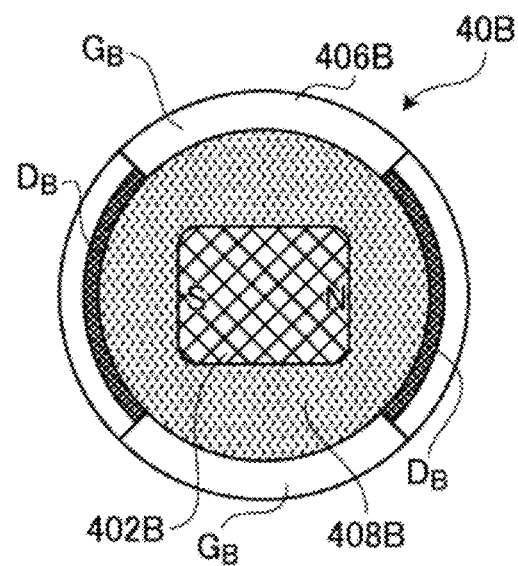

FIGS. 4a to 4d show a sensor 40B according to Embodiment 2 of the present invention. FIGS. 4a, 4b are a plan view and a front view of the sensor 40B, respectively. FIG. 4c is a sectional view along the line $A_B$-$A_B$ in FIG. 4a. FIG. 4d is a sectional view along the line $B_B$-$B_B$ in FIG. 4b. The same description as for previous embodiments will be hereinafter simplified or omitted.

As shown in FIGS. 4a to 4d, the sensor 40B includes a permanent magnet 402B, a box-shaped electrode 404B (a first electrode), a box-shaped electrode 406B (a second electrode), and a retaining member 408B (a magnet covering member). As shown in FIG. 4c, a signal line 41 is connected to the box-shaped electrode 404B, and a signal line 42 is connected to the box-shaped electrode 406B. The magnet covering member may inhibit accumulation of the magnetic powder.

The box-shaped electrodes 404B and 406B are cylindrical members having a blocked opening on one axial end side thereof (in other words, these box-shaped electrodes are opened only on the other end side thereof). The box-shaped electrode 404B is arranged with the opening thereof opposed to the box-shaped electrode 406B. The box-shaped electrode 406B is arranged with the opening thereof opposed to the box-shaped electrode 404B such that the opening of the box-shaped electrode 406B is opposed to the opening of the box-shaped electrode 404B.

The retaining member 408B has a columnar shape with an outer diameter slightly smaller than the inner diameter of the box-shaped electrodes 404B and 406B and is housed in the hollow portions of the box-shaped electrodes 404B and 406B. The retaining member 408B is disposed in a space defined by the inner wall surface.

The box-shaped electrode 404B and the box-shaped electrode 406B are disposed such that the annular opposing surfaces thereof (denoted by signs 404Bc and 406Bc in FIG. 4c) are spaced apart from each other by a predetermined distance. Since the opposing surfaces are spaced apart from each other, there is an annular gap $G_B$ between the opposing surfaces, and the gap $G_B$ surrounds the axially middle portion of the retaining member 408B.

The permanent magnet 402B is disposed such that the S-pole and the N-pole thereof are arranged in the direction of the arrow MB shown in FIG. 4c. The permanent magnet 402B is embedded in the retaining member 408B such that the line connecting between the magnetic poles is perpendicular to the central axis of the retaining member 408B and intersects the gap $G_B$. Therefore, the magnetic field is selectively applied to the region shaded deeply in FIGS. 4c and 4d within the gap $G_B$ extending over the entire periphery of the side surface of the retaining member 408B, and this region is the sensing region in Embodiment 2. This sensing region will be hereinafter referred to as "the sensing region $D_B$."

The non-sensing region outside the sensing region $D_B$ is not positioned in the magnetic flux path and is spaced apart from the magnetic poles of the permanent magnet 402B. Therefore, almost no magnetic flux passes in the non-sensing region, while intensive magnetic flux passes in the sensing region $D_B$. Accordingly, almost no abrasion powder is attracted onto the region other than the sensing region $D_B$.

Thus, in Embodiment 2, the permanent magnet 402B and the gap $G_B$ are disposed in an appropriate positional relationship, so as to selectively set a limited region in the gap $G_B$ as the sensing region $D_B$. Since a stable amount of abrasion powder is attracted concentratedly onto the sensing region $D_B$, the outputs from the sensor 40B are stable. Therefore, the superior control device can sense the increase of the produced abrasion powder reliably (with a high reliability).

Further, in Embodiment 2, not only the sensing region $D_B$ but the entire gap $G_B$ is exposed outside. Since there are fewer structures surrounding the sensing region $D_B$ than in Embodiment 1, the abrasion powder attracted toward the sensing region $D_B$ is less apt to be blocked by these structures and tends to be attracted onto the sensing region $D_B$.

The shapes of the permanent magnet 402B and the box-shaped electrodes 404B and 406B and the positional relationship between them are not limited to those shown in FIGS. 4a to 4d. Any other shapes or positional relationships may be substituted such that the abrasion powder is concentratedly attracted onto only a part of the region within the gap $G_B$.

In this embodiment, the sensor 40B is thus configured such that the abrasion powder is restrained by the magnetic flux and accumulated only in the sensing region $D_B$, not attracted onto the outer surface of the sensor 40B, by adjusting the shapes, sizes, and arrangements of the permanent magnet 402B and the box-shaped electrodes 404B and 406B. Further, it is also possible that the permanent magnet 402B is a magnet or an electromagnet. The box-shaped electrodes 404B and 406B are not limited to a box-like shape but may be a disk or a circular arc formed only in the sensing region $D_B$.

Embodiment 3

Figure 5A:
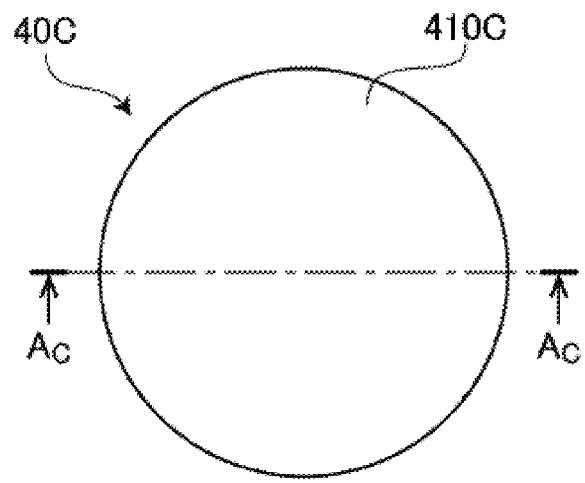
FIGS. 5a to 5d show a sensor according to Embodiment 3 of the present invention.
Figure 5B:
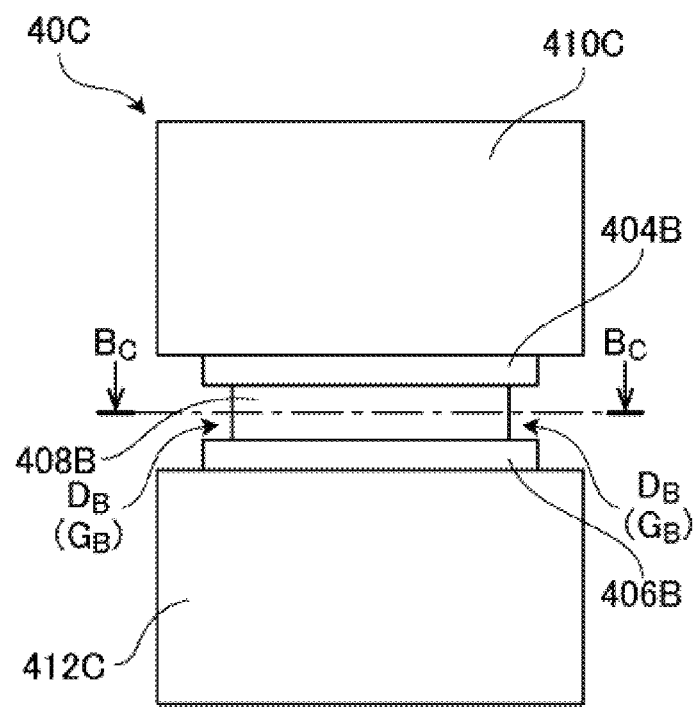
Figure 5C:
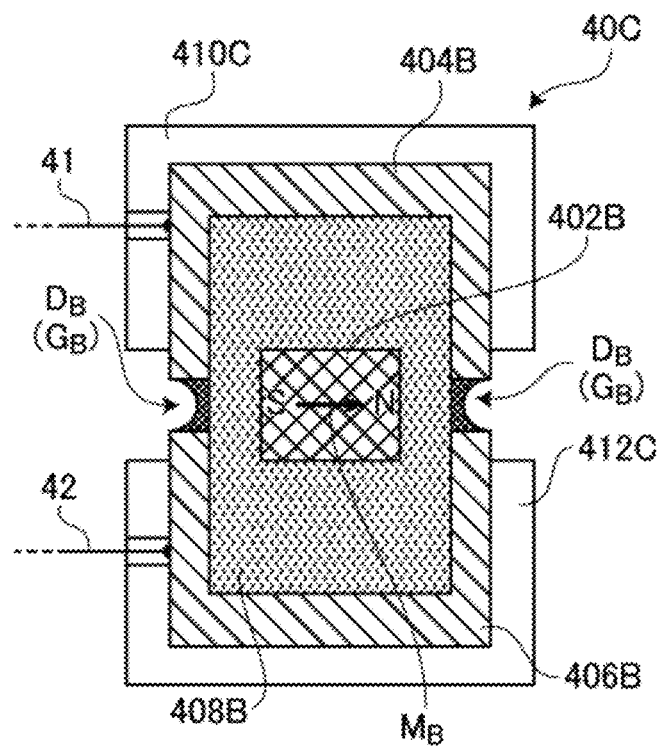
Figure 5D:
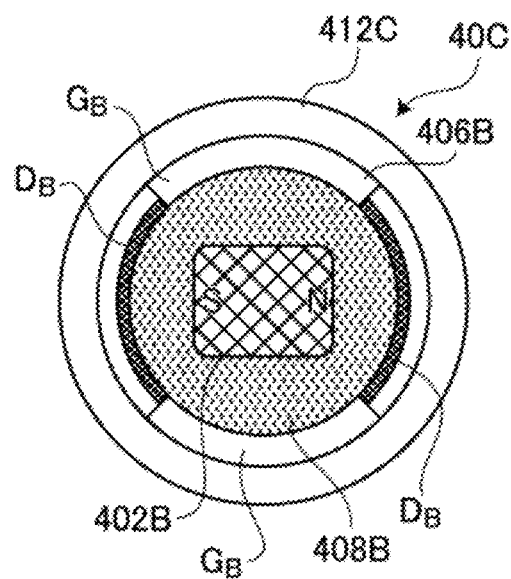

FIGS. 5a to 5d show a sensor 40C according to Embodiment 3 of the present invention. FIGS. 5a, 5b are a plan view and a front view of the sensor 40C, respectively. FIG. 5c is a sectional view along the line $A_c$-$A_c$ in FIG. 5a. FIG. 5d is a sectional view along the line $B_c$-$B_c$ in FIG. 5b.

As shown in FIGS. 5a to 5d, the sensor 40C according to Embodiment 3 is formed by mounting protection members 410C and 412C made of a resin to the sensor 40B according to Embodiment 2, so as to increase the ease of handling of the sensor 40C as a part (the insulation quality). This arrangement inhibits an operator from touching the electrodes and receiving an electric shock.

The protection members 410C, 412C cover the entire outer surfaces of the box-shaped electrodes 404C, 406C, respectively. The distance between the opposed end surfaces of the protection member 410C and the protection member 412C is equal to or greater than the width of the gap $G_B$, such that the abrasion powder attracted toward the sensing region $D_B$ is not blocked. In other words, the protection member 410C and the protection member 412C form an opening in a region including at least the entirety of the gap $G_B$.

In Embodiment 3, since a stable amount of abrasion powder is attracted concentratedly onto the sensing region $D_B$, the outputs from the sensor 40C are stable. Therefore, the superior control device can sense the increase of the produced abrasion powder reliably (with a high reliability).

Embodiment 4

Figure 6A:
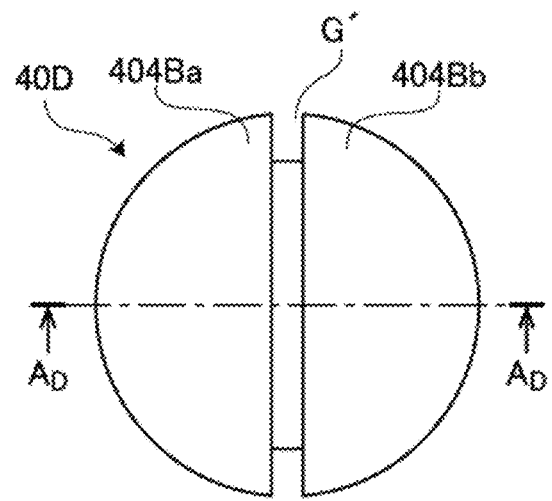
FIGS. 6a to 6d show a sensor according to Embodiment 4 of the present invention.
Figure 6B:
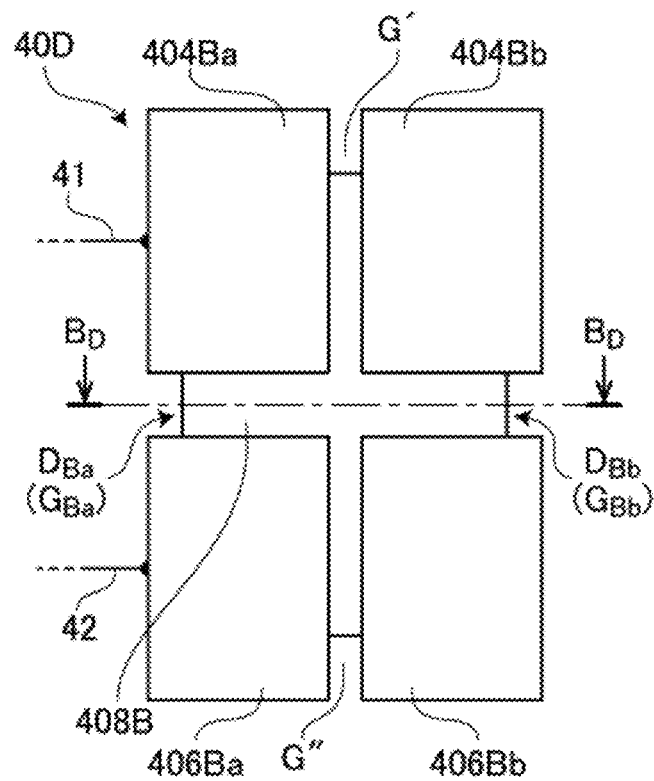
Figure 6C:
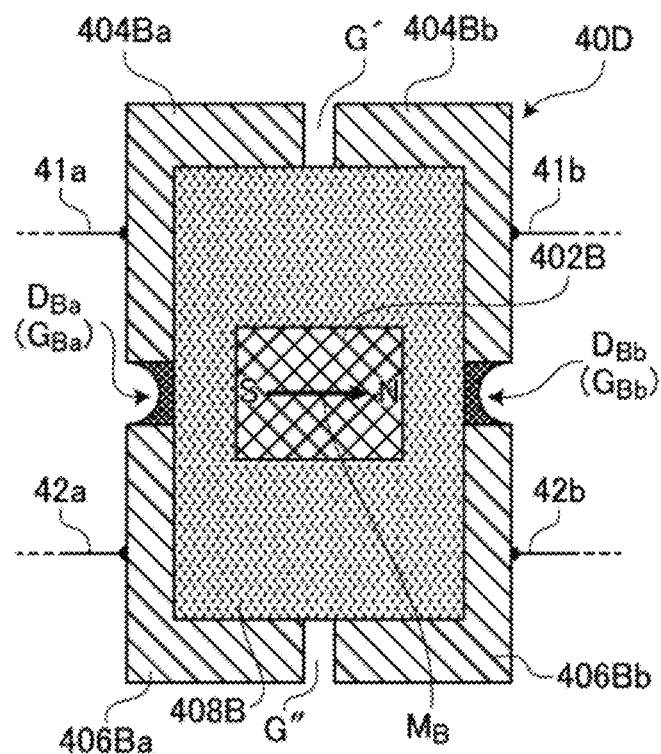
Figure 6D:
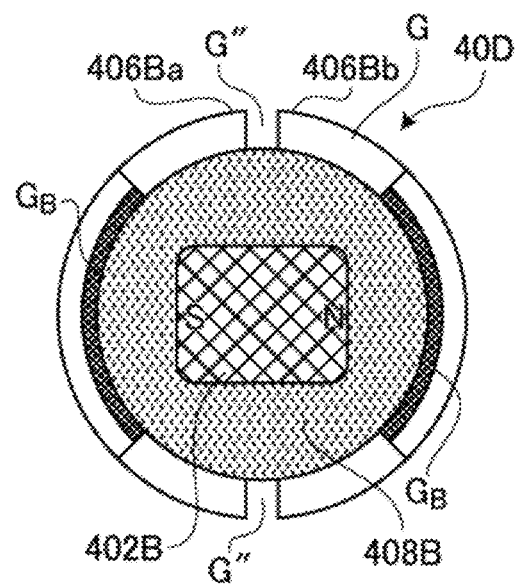

FIGS. 6a to 6d show a sensor 40D according to Embodiment 4 of the present invention. FIGS. 6a, 6b are a plan view and a front view of the sensor 40D, respectively. FIG. 6c is a sectional view along the line $A_D$-$A_D$ in FIG. 6a. FIG. 6d is a sectional view along the line $B_D$-$B_D$ in FIG. 6b.

As shown in FIGS. 6a to 6d, the sensor 40D includes a permanent magnet 402B, a box-shaped electrode 404Ba (a first electrode), a box-shaped electrode 404Bb (a first electrode), a box-shaped electrode 406Ba (a second electrode), a box-shaped electrode 406Bb (a second electrode), and a retaining member 408B. In this embodiment, two pairs of output lines (signal lines 41a, 41b and signal lines 42a, 42b) are connected to the sensor 40D. As shown in FIG. 6c, the signal lines 41a, 41b, 42a, 42b are connected to the box-shaped electrodes 404Ba, 404Bb, 406Ba, 406Bb, respectively.

The sensor 40D according to Embodiment 4 is formed by configuring the sensor 40B according to Embodiment 2 such that the box-shaped electrode 404B is divided into two electrodes (the box-shaped electrodes 404Ba, 404Bb) and the box-shaped electrode 406B is divided into two electrodes (the box-shaped electrodes 406Ba, 406Bb). A gap G' is formed between the box-shaped electrode 404Ba and the box-shaped electrode 404Bb. A gap G" is formed between the box-shaped electrode 406Ba and the box-shaped electrode 406Bb.

When a mechanical device such as the speed reducer 20 is worked, a foreign matter (for example, a cutting chip) having a large particle diameter may be produced and enter an oil bath 10. When this kind of foreign matter is attracted onto the gap $G_{Ba}$, a short circuit may occur between the electrodes and vary the output levels of the output lines. As a result, an increase of the amount of produced abrasion powder may be erroneously sensed even when almost no abrasion powder has been produced.

To overcome this drawback, the sensor 40D according to Embodiment 4 has a gap $G_{Bb}$ in addition to a gap $G_{Ba}$. The sensor 40D according to Embodiment 4 may be configured such that, when short circuits between electrodes occur at all the gaps (the gaps $G_{Ba}$, $G_{Bb}$), a sensing signal is transmitted or the superior control device determines that the amount of abrasion powder has increased. This configuration inhibits erroneous sensing caused by disturbance (for example, a cutting chip having a large particle diameter), and the superior control device can sense the increase of the produced abrasion powder reliably (with a high reliability). In case of the digital sensing, the increase of produced abrasion powder may be determined when short circuit signals (On signals) are sensed for both the sensing region $D_{Ba}$ and the sensing region $D_{Bb}$.

Embodiment 5

Figure 7A:
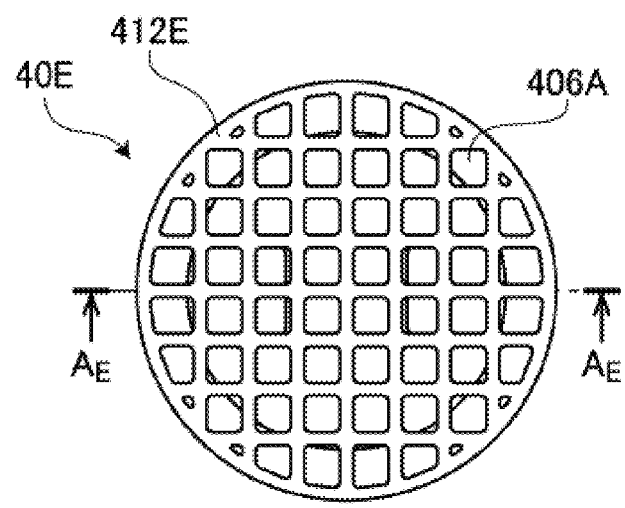
FIGS. 7a to 7e show a sensor according to Embodiment 5 of the present invention.
Figure 7B:
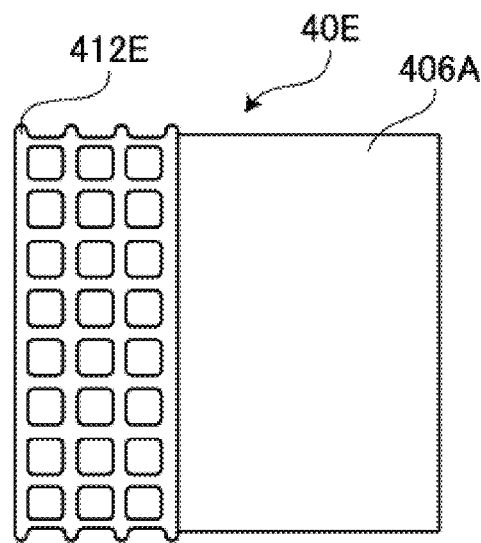
Figure 7C:
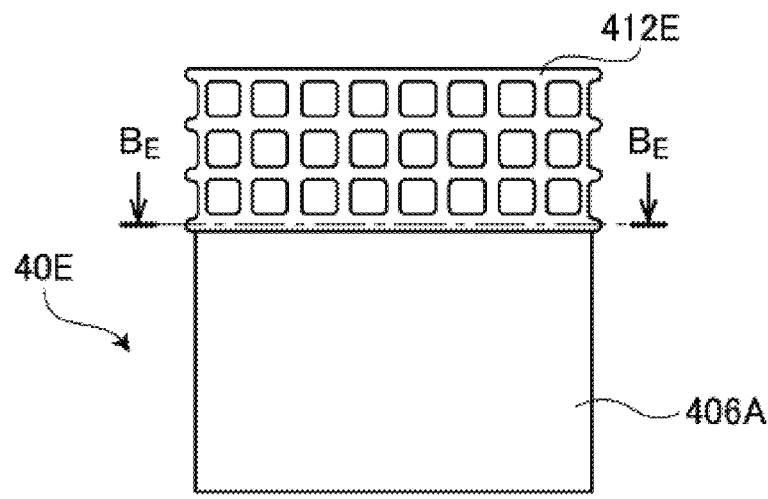
Figure 7D:
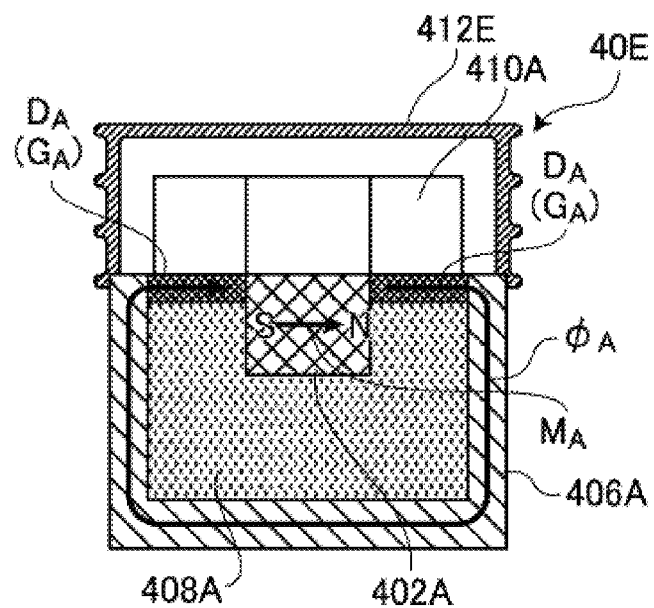
Figure 7E:
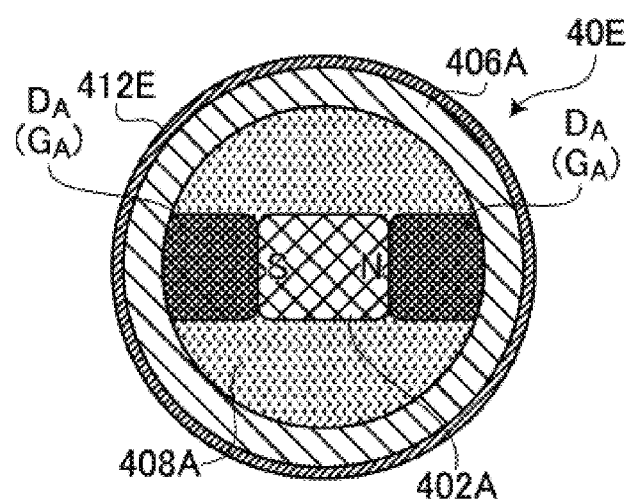

FIGS. 7a to 7e show a sensor 40E according to Embodiment 5 of the present invention. FIGS. 7a, 7b, 7c are a plan view, a right side view, and a front view of the sensor 40E, respectively. FIG. 7d is a sectional view along the line $A_E$-$A_E$ in FIG. 7a. FIG. 7e is a sectional view along the line BE-BE in FIG. 7c.

The sensor 40E is formed by mounting a mesh cover 412E (a filter member) to the sensor 40A according to Embodiment 1.

The mesh cover 412E covers the entirety of the gap $G_A$ (and the jacket member 410A). This prevents a cutting chip or abrasion powder having a particle size larger than the mesh size from being undesirably attracted onto the sensing region $D_A$. As a result, the robustness of the sensor 40E is increased.

In Embodiment 5, since a stable amount of fine abrasion powder is attracted concentratedly onto the sensing region $D_A$, the outputs from the sensor 40E are more stable. Therefore, the superior control device can sense the increase of the produced abrasion powder reliably (with a high reliability).

Embodiment 6

Figure 8A:
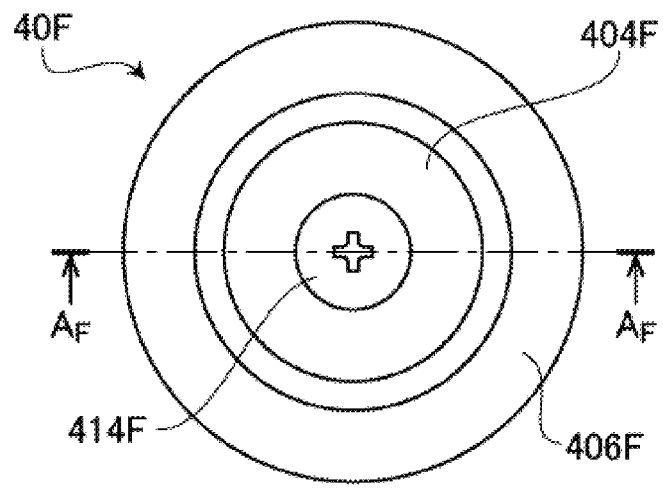
FIGS. 8a to 8d show a sensor according to Embodiment 6 of the present invention.
Figure 8B:
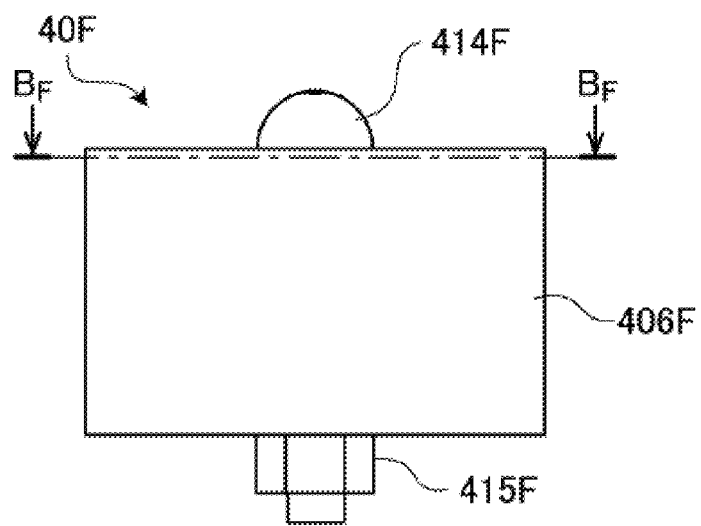
Figure 8C:
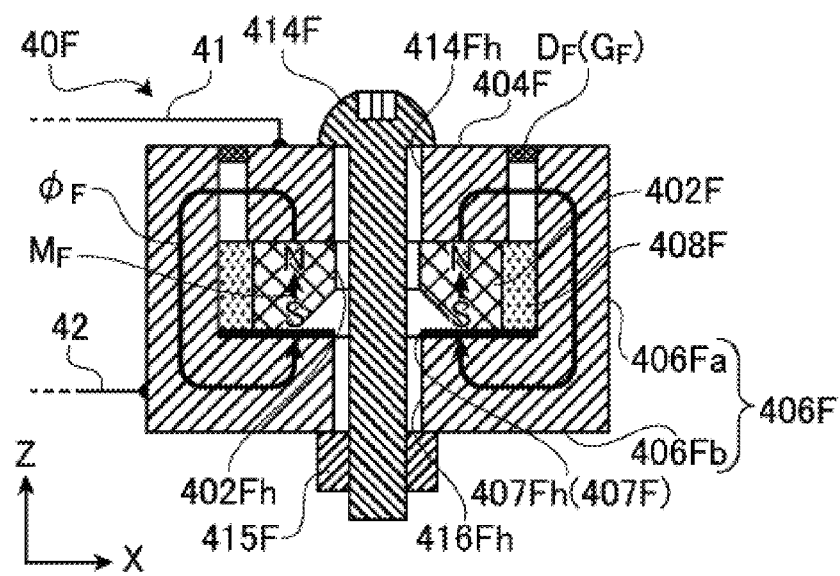
Figure 8D:
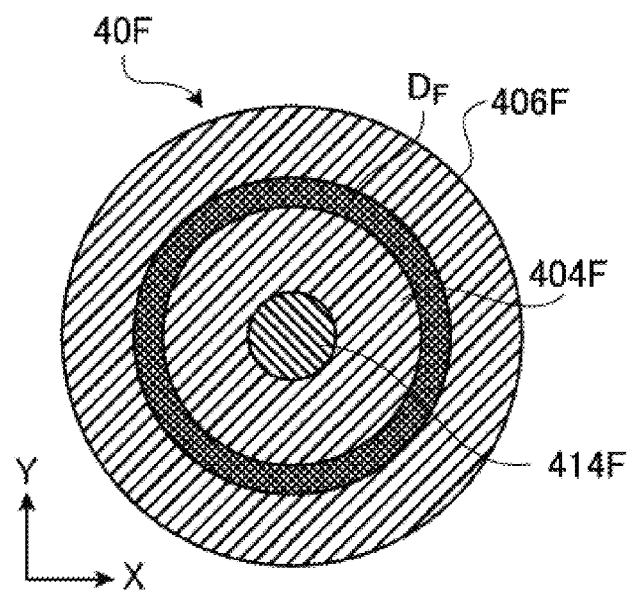

FIGS. 8a to 8d show a sensor 40F according to Embodiment 6 of the present invention. FIG. 8a is a plan view of the sensor 40F, and FIG. 8b is a front view of the same. FIG. 8c is a sectional view along the line $A_F$-$A_F$ in FIG. 8a, and FIG. 8d is a sectional view along the line $B_F$-$B_F$ in FIG. 8c.

The sensor 40F includes a permanent magnet 402F, a box-shaped electrode 406F (a second electrode), a cap-shaped electrode 404F (a first electrode), a retaining member 408B, an insulating sheet 407F, an external screw 414F, and a nut 415F. As shown in FIG. 8c, a signal line 41 is connected to the cap-shaped electrode 404F, and a signal line 42 is connected to the box-shaped electrode 406F.

The box-shaped electrode 406F and the cap-shaped electrode 404F are magnetic members formed of a magnetic material having electric conductivity.

The box-shaped electrode 406F has a cylindrical box-like shape (a bottomed cylindrical shape) including a side wall portion 406Fa having a cylindrical shape and a bottom portion 406Fb having a disk-like shape and blocking an opening of the side wall portion 406Fa on one axial end side thereof (the lower side). In the middle of the bottom portion 406Fb, there is concentrically formed a through-hole 416Fh through which the shaft of the external screw 414F is inserted.

The cap-shaped electrode 404F has a substantially disk-like shape, and in the middle of the cap-shaped electrode 404F, there is concentrically formed a through-hole 414Fh through which the shaft of the external screw 414F is inserted. The outer diameter of the cap-shaped electrode 404F is smaller than the inner diameter of the side wall portion 406Fa of the box-shaped electrode 406F. Between the outer peripheral surface of the cap-shaped electrode 404F and the inner peripheral surface of the box-shaped electrode 406F, there is formed a hollow portion (a gap $G_F$) having an annular shape and communicating with the outer space (the oil bath 20B) outside the sensor 40F.

The permanent magnet 402F has a substantially disk-like shape, and in the middle of the permanent magnet 402F, there is concentrically formed a through-hole 402Fh through which the shaft of the external screw 414F is inserted.

The retaining member 408F has a cylindrical shape and is formed of the same resin (non-magnetic material) as the retaining member 408A in Embodiment 1. In the retaining member 408F, there is concentrically embedded the box-shaped electrode 406F. The outer diameter of the retaining member 408F is slightly smaller than the inner diameter of the side wall portion 406Fa of the box-shaped electrode 406F, and the retaining member 408F is concentrically disposed on the bottom of the hollow portion of the box-shaped electrode 406F. Thus, the permanent magnet 402F is positioned concentrically in the hollow portion of the box-shaped electrode 406F and retained by the retaining member 408F. The height (the length in the axial direction) of the retaining member 408F is equal to the height of the permanent magnet 402F, and the top surface of the retaining member 408F is substantially flush with the top surface of the permanent magnet 402F.

The insulating sheet 407F is a tabular member formed of paper, resin, or the like and having an electrical insulating quality. The insulating sheet 407F has a circular shape with an outer diameter larger than that of the permanent magnet 402F, and in the middle of the insulating sheet 407F, there is concentrically formed a through-hole 407Fh through which the shaft of the external screw 414F is inserted. The insulating sheet 407F is placed on the bottom portion 406Fb of the box-shaped electrode 406F and electrically insulates the box-shaped electrode 406F from the permanent magnet 402F.

The external screw 414F and the nut 415F are non-magnetic members formed of a resin and having an electrical insulating quality.

The sensor 40F is fabricated by placing the insulating sheet 407F on the bottom portion 406Fb of the box-shaped electrode 406F, placing thereon the retaining member 408F and the permanent magnet 402F, placing thereon the cap-shaped electrode 404F, inserting the shaft of the external screw 414F through the through-holes 404Fh, 406Fh, 407Fh, 408Fh into the nut 415F, and fastening integrally the box-shaped electrode 406F, the insulating sheet 407F, the permanent magnet 402F, the retaining member 408F, and the cap-shaped electrode 404F with the external screw 414F and the nut 415F.

The permanent magnet 402F is magnetized in the direction of the arrow $M_F$ in FIG. 8c, so as to form a magnetic flux path in the sensor 40F that is shown by the arrow $\varphi_F$ in FIG. 8c and passing the gap $G_F$. In this embodiment, the magnetic flux $\varphi_F$ is radiated from the entire periphery of the outer peripheral surface of the cap-shaped electrode 404F, and the entire circumference of the annular gap $G_F$ is set as the sensing region $D_F$.

The sum of the heights of the insulating sheet 407F, the permanent magnet 402F, and the cap-shaped electrode 404F stacked together in the axial direction in the hollow portion of the box-shaped electrode 406F is equal to the depth of the hollow portion of the box-shaped electrode 406F. Therefore, after fabrication, the top surface of the cap-shaped electrode 404F is flush with the top end surface of the box-shaped electrode 406F. Further, the sensor 40F is configured, by adjusting the shape, size, and arrangement of the cap-shaped electrode 404F and the box-shaped electrode 406F, such that the magnetic flux $\varphi_F$ perpendicularly passes the outer peripheral surface of the cap-shaped electrode 404F, runs straight in the gap $G_F$, and perpendicularly enters the inner peripheral surface of the box-shaped electrode 406F. Therefore, the magnetic flux $\varphi_F$ hardly leaks out of the magnetic flux path $\varphi_F$. The abrasion powder is restrained by the magnetic flux $\varphi_F$ and accumulated only in the sensing region $D_F$, not attracted onto the outer surface of the sensor 40F. That is, the abrasion powder is inhibited from being accumulated in regions other than the sensing region $D_F$ and is allowed to be accumulated concentratedly in the sensing region $D_F$, resulting in a high sensitivity in sensing. Further, since the sensing region $D_F$ has a circumferential shape, a large amount of abrasion powder can be accumulated in the sensing region $D_F$, and the damage to devices such as the speed reducer caused by the abrasion powder can be reduced.

Embodiment 7

Figure 9A:
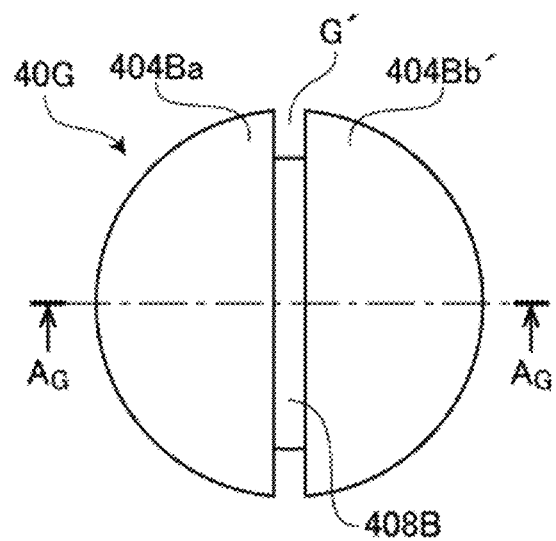
FIGS. 9a to 9d show a sensor according to Embodiment 7 of the present invention.
Figure 9B:
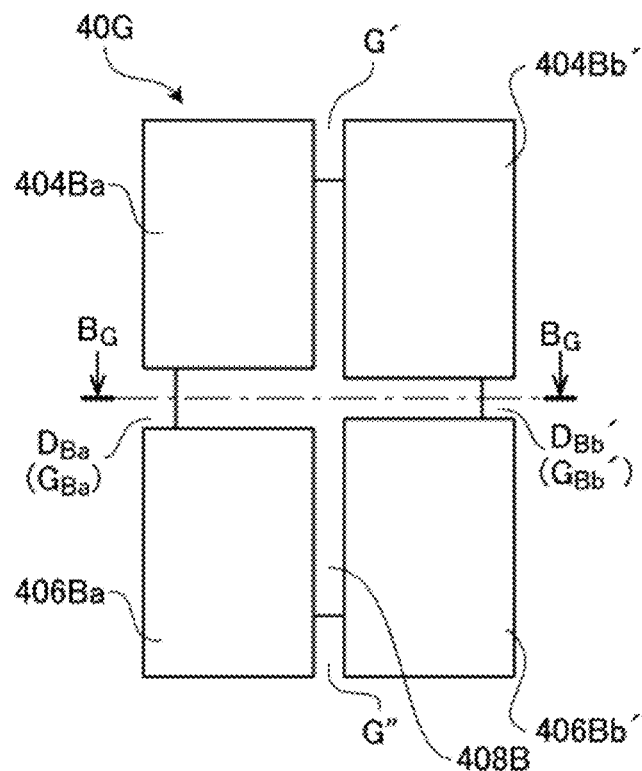
Figure 9C:
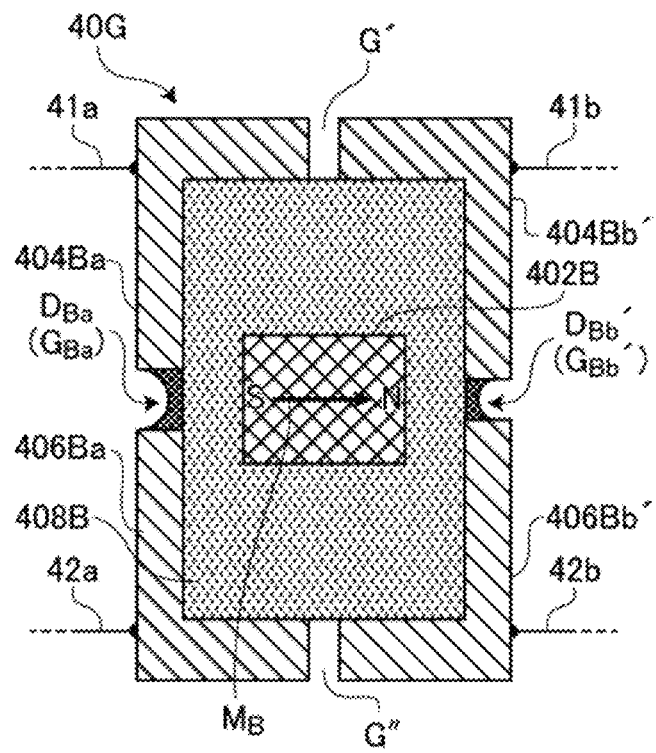
Figure 9D:
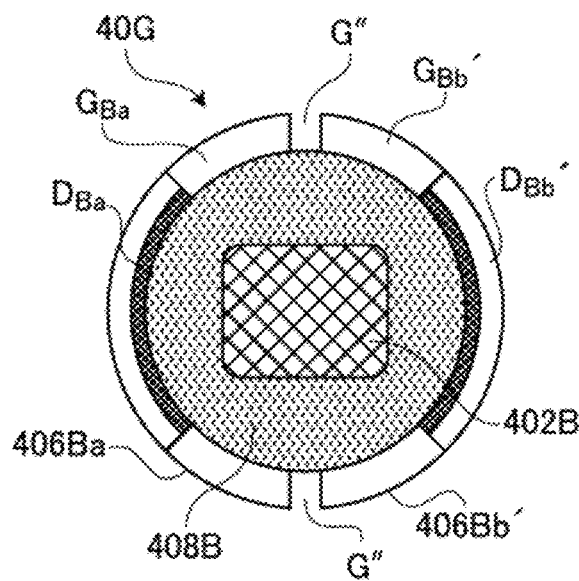

FIGS. 9a to 9d show a sensor 40G according to Embodiment 7 of the present invention. FIG. 9a is a plan view of the sensor 40G, and FIG. 9b is a front view of the same. FIG. 9c is a sectional view along the line $A_G$-$A_G$ in FIG. 9a, and FIG. 9d is a sectional view along the line $B_G$-$B_G$ in FIG. 9b.

The sensor 40G is a modification of the sensor 40D of Embodiment 4 (specifically, the box-shaped electrodes 404Bb and 406Bb are modified). In the sensor 40D of Embodiment 4, the box-shaped electrodes 404Ba and 404Bb have the same length in the Z-axis direction, and the box-shaped electrodes 406Ba and 406Bb have the same length in the Z-axis direction. Therefore, the gap $G_{Ba}$ between the box-shaped electrode 404Ba and the box-shaped electrode 406Ba has the same gap length (the distance between electrodes on the gap) as the gap $G_{Bb}$ between the box-shaped electrode 404Bb and the box-shaped electrode 406Bb. By contrast, in this embodiment, the box-shaped electrode 404Bb' has a larger length in the Z-axis direction than the box-shaped electrode 404Ba, and the box-shaped electrode 406Bb' has a larger length in the Z-axis direction than the box-shaped electrode 406Ba. Therefore, the gap $G_{Bb'}$ between the box-shaped electrode 404Bb' and the box-shaped electrode 406Bb' has a smaller gap length than the gap $G_{Ba}$ between the box-shaped electrode 404Ba and the box-shaped electrode 406Ba.

In this embodiment, as described above, the gap $G_{Bb'}$ has a smaller gap length than the gap $G_{Ba}$, and therefore, the sensing region $D_{Bb'}$ conducts electricity earlier than the sensing region $D_{Ba}$ because the sensing region $D_{Bb'}$ requires a smaller amount of abrasion powder for conducting electricity between the electrodes. That is, in this embodiment, each of the positive electrode and the negative electrode (the box-shaped electrode 404B and the box-shaped electrode 406B) is divided into two pieces to provide two pairs of electrodes, and the gaps between the electrodes have different gap lengths, so as to provide two different threshold values of the amount of the abrasion powder enough to conduct electricity between the electrodes (in other words, two different timings at which electricity begins to be conducted). Use of such a sensor makes it possible to sense the increase of the abrasion powder stepwise, and therefore, the progress of wear of the parts of the speed reducer can be grasped in more detail, and the failure of the speed reducer can be predicted more accurately.

Embodiment 8

Figure 10A:
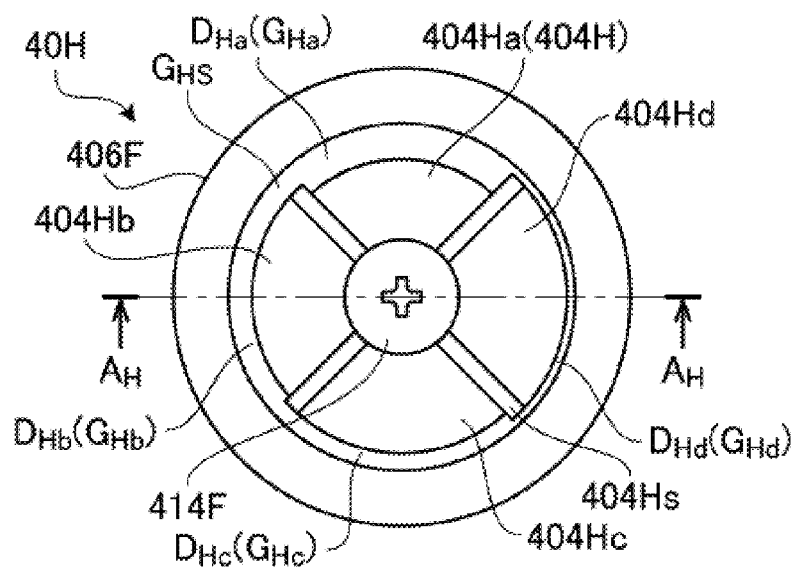
FIGS. 10a to 10d show a sensor according to Embodiment 8 of the present invention.
Figure 10B:
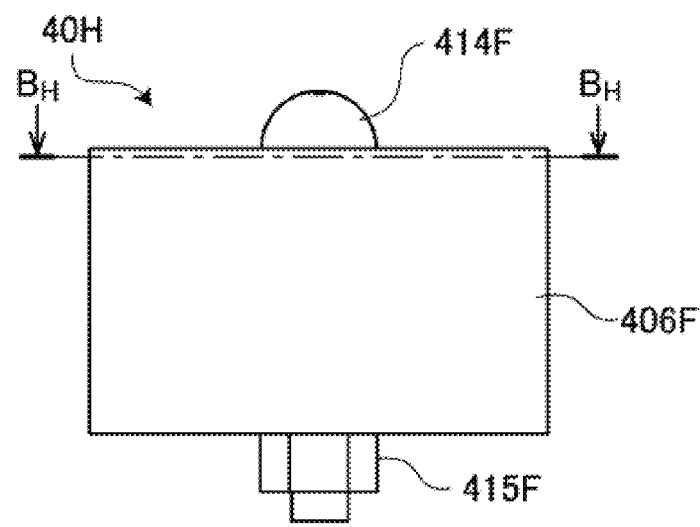
Figure 10C:
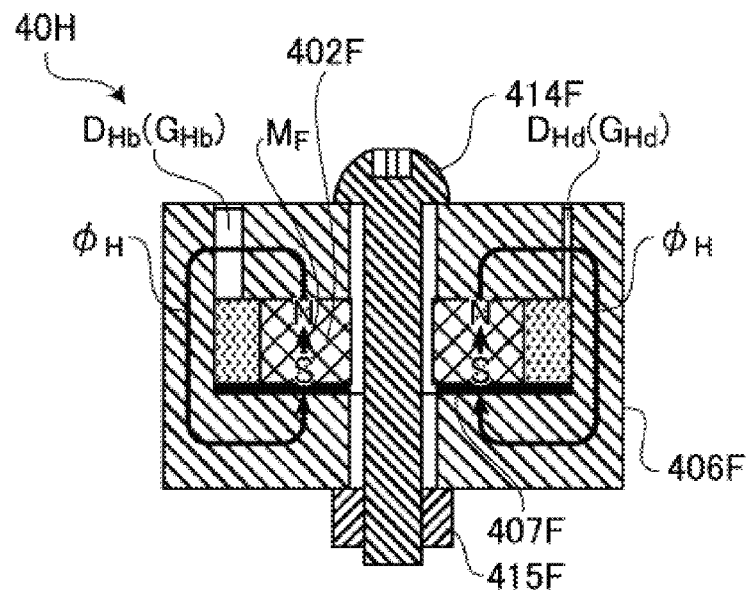
Figure 10D:
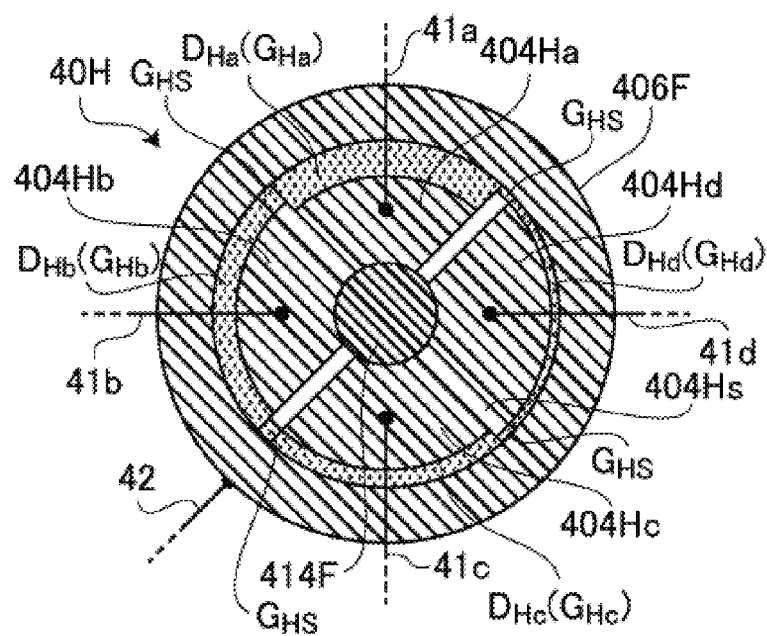

FIGS. 10a to 10d show a sensor 40H according to Embodiment 8 of the present invention. FIG. 10a is a plan view of the sensor 40H, and FIG. 10b is a front view of the same. FIG. 10c is a sectional view along the line $A_H$-$A_H$ in FIG. 10a, and FIG. 10d is a sectional view along the line $B_H$-$B_H$ in FIG. 10b.

The sensor 40H is a modification of the sensor 40F of Embodiment 6 (specifically, the cap-shaped electrode 404F is modified) such that the increase of the abrasion powder can be sensed stepwise as in the sensor 40G of Embodiment 7.

The cap-shaped electrode 404H of this embodiment includes four electrodes 404Ha, 404Hb, 404Hc, 404Hd and four spacers 404Hs. The electrodes 404Ha to 404Hd are magnetic members provided by dividing the cap-shaped electrode 404F of Embodiment 6 having a disk-like shape into four sectors. The radii of the electrodes 404Ha, 404Hb, 404Hc, 404Hd increase in this order stepwise (for example, in arithmetical proportion). In this embodiment, the output lines include one signal line 42 (a grounding wire) and four signal lines 41a, 41b, 41c, 41d. As shown in FIG. 10d, the signal line 42 is connected to the electrode 406F, and the signal lines 41a, 41b, 41c, 41d are connected to the electrodes 404Ha, 404Hb, 404Hc, 404Hd, respectively.

The spacers 404Hs are tabular members formed of a non-magnetic material having an electrical insulating quality such as a resin or ceramic. The four electrodes 404Ha to 404Hd are adhered to each other with an adhesive in the circumferential direction with the spacers 404Hs interposed therebetween.

Thus, the radii of the cap-shaped electrodes 404H vary stepwise in the circumferential direction, and therefore, the gap length of the gap $G_F$ between the outer peripheral surfaces of the cap-shaped electrodes 404H and the inner peripheral surface of the box-shaped electrode 406F also varies stepwise in the circumferential direction. The gap $G_F$ is divided into gaps $G_{Ha}$, $G_{Hb}$, $G_{Hc}$, $G_{Hd}$ adjacent to the electrodes 404Ha, 404Hb, 404Hc, 404Hd, respectively and four gaps $G_{Hs}$ adjacent to the spacers 404Hs. Since the magnetic flux pi passes the entireties of the gaps $G_{Ha}$, $G_{Hb}$, $G_{Hc}$, $G_{Hd}$, these gaps constitute the sensing regions $D_{Ha}$, $D_{Hb}$, $D_{Hc}$, $D_{Hd}$, respectively. The magnetic flux $\varphi_H$ for accumulating the abrasion powder does not pass the gaps $G_{Hs}$, and therefore, these gaps constitute non-sensing regions.

The gap lengths of the gaps $G_{Ha}$, $G_{Hb}$, $G_{Hc}$, $G_{Hd}$ (the sensing regions $D_{Ha}$, $D_{Hb}$, $D_{Hc}$, $D_{Hd}$) decrease in this order in arithmetical proportion. Also, the amounts of accumulated abrasion powder required for conducting electricity between electrodes decrease in this order. Accordingly, electricity begins to be conducted between the electrodes in the reverse order, that is, in the order of the sensing regions $D_{Ha}$, $D_{Hc}$, $D_{Hb}$, $D_{Ha}$. The sensor 40H of this embodiment can sense the increase of the abrasion powder stepwise at four levels, which is a greater number than in the sensor 40G of Embodiment 7, and therefore, the progress of wear of the parts of the speed reducer can be grasped in further detail, and the failure of the speed reducer can be predicted further accurately.

In this embodiment, the cap-shaped electrode 404F is divided into four electrodes 404Ha to 404Hd. It is also possible to divide the cap-shaped electrode 404F into two electrodes, three electrodes, or five or more electrodes.

The examples of the embodiments of the present invention have been described above. The embodiments of the present invention are not limited to the above examples but can be modified variously within the scope of the technical idea of the present invention. For example, the embodiments of the present invention include combinations of the above examples described herein and obvious embodiments.

For example, the sensor 40 in the above embodiments is installed in a speed reducer included in a turning portion of a turning barrel or an arm joint of an industrial robot 1. In other embodiments, the sensor 40 may be installed in a speed reducer included in a turning portion of other machine tools.

The sensor 40 may be installed in other types of speed reducers such as a planetary gear speed reducer, in addition to the oscillating speed reducer shown in FIG. 2.

The sensor 40 may be used for mechanical devices other than speed reducers. By way of an example, the sensor 40 may be used as a check sensor for checking the uncleanness of an engine oil.

In Embodiment 1 described above, a part of the gap $G_A$ is covered with the jacket member 410A (a covering member) to provide a non-sensing region. It is also possible to cover a part of the gap with a magnetism shield member (for example, a net made of a ferromagnetic material such as iron and coated with a resin) to magnetically shield the part from the outer space, thereby providing a non-sensing region.

What is claimed is:

1. A sensor for sensing reduction of electric resistance between a first electrode and at least one second electrode, a magnetic field being applied between the first electrode and said at least one second electrode to accumulate magnetic powder floating in a lubricant between the first electrode and said at least one second electrode,
   wherein the first electrode comprises a magnet producing the magnetic field;
   wherein at least one sensing region in which the magnetic powder is to be accumulated is provided in at least a part of a region between the first electrode and said at least one second electrode, and
   wherein the magnetic powder is inhibited from being accumulated in a non-sensing region constituted by a space around the first electrode and said at least one second electrode other than the at least one sensing region.

2. The sensor of claim 1,
   wherein at least one gap is provided between the first electrode and the at least one second electrode, and
   wherein the at least one gap includes the at least one sensing region to which the magnetic field is applied.

3. The sensor of claim 2, further comprising a magnet producing the magnetic field.

4. The sensor of claim 1, further comprising a covering member that covers the first electrode and said at least one second electrode to inhibit the magnetic powder from being accumulated in the non-sensing region.

5. The sensor of claim 1, wherein an entire periphery of the magnet is covered with a magnet covering member.

6. The sensor of claim 1, wherein the magnetic field is selectively applied to the at least one sensing region.

7. The sensor of claim 1, wherein the at least one sensing region comprises a plurality of sensing regions.

8. The sensor of claim 7, wherein the plurality of sensing regions comprise a first sensing region and a second sensing region,
   wherein the first sensing region is provided adjacent to an N-pole of the magnet, and
   wherein the second sensing region is provided adjacent to an S-pole of the magnet.

9. The sensor of claim 7, wherein the at least one second electrode comprises a plurality of second electrodes,
   wherein the at least one gap comprises a plurality of gaps provided between the first electrode and each of the plurality of second electrodes, and
   wherein each of the plurality of gaps includes one of the plurality of sensing regions.

10. The sensor of claim 9, wherein the plurality of sensing regions have different gap lengths.

11. The sensor of claim 7, further comprising a plurality of pairs of the first and second electrodes,
    wherein the plurality of pairs of the first and second electrodes have different gap lengths.

12. The sensor of claim 1, wherein a narrow recess is provided in an outer periphery of the sensor, and
    wherein the at least one sensing region is provided deep in the recess.

13. The sensor of claim 1, further comprising a filter member disposed between the at least one sensing region and an outer space, the filter member blocking foreign matter having a large particle diameter.

14. The sensor of claim 1, wherein the sensor is configured such that magnetic flux is prevented from leaking out of the at least one sensing region.

15. The sensor of claim 14, wherein the at least one sensing region is interposed between a first plane formed on the first electrode and a second plane formed on the at least one second electrode and opposed in parallel to the first plane, and wherein the magnetic flux intersects the first plane and the second plane perpendicularly in the at least one sensing region.

\* \* \* \* \*